United States Patent [19]

Ward

[11] Patent Number: 5,081,122
[45] Date of Patent: Jan. 14, 1992

[54] ANTIGLAUCOMA COMPOSITIONS CONTAINING 4-ARYLCARBONYL-1-(4-MORPHOLINYL)-LOWER-ALKYL)-1H-INDOLES AND METHOD OF USE THEREOF

[75] Inventor: Susan J. Ward, East Greenbush, N.Y.

[73] Assignee: Sterling Drug Inc., New York, N.Y.

[21] Appl. No.: 489,311

[22] Filed: Mar. 5, 1990

[51] Int. Cl.$^5$ .......................................... A61K 31/535
[52] U.S. Cl. .................................. 514/235.2; 514/913
[58] Field of Search .................. 514/231.5, 235.2, 913

[56] References Cited

U.S. PATENT DOCUMENTS

Re. 32,761  8/1988  Bell ........................................ 514/210
3,946,029   3/1976  Descamps et al. .
4,840,950   6/1989  D'Ambra ........................... 514/235.2

OTHER PUBLICATIONS

Croce, Ann. di Chim. 63,29–35 (1973).

Primary Examiner—Frederick E. Waddell
Assistant Examiner—Zohreh A. Fay
Attorney, Agent, or Firm—William G. Webb; Paul E. Dupont; Theodore C. Miller

[57] ABSTRACT

Antiglaucoma compositions containing 3-R$_3$-4-arylcarbonyl-1-[(4-morpholinyl)-lower-alkyl]-1H-indoles and a method of use thereof in the treatment of glaucoma.

9 Claims, No Drawings

ANTIGLAUCOMA COMPOSITIONS CONTAINING 4-ARYLCARBONYL-1-(4-MORPHOLINYL)-LOWER-ALKYL)-1H-INDOLES AND METHOD OF USE THEREOF

BACKGROUND OF THE INVENTION

This invention relates to antiglaucoma compositions containing 3-$R_3$-4-arylcarbonyl-1-[(4-morpholinyl)-loweralkyl]-1H-indoles and the method of use thereof in reducing intraocular pressure.

INFORMATION DISCLOSURE STATEMENT

Bell U.S. Pat. No. 4,581,354 discloses 3-arylcarbonyl-1-(amino-lower-alkyl)-1H-indoles useful as analgesic, anti-rheumatic and anti-inflammatory agents.

Deschamps et al. U.S. Pat. No. 3,946,029 discloses 1-(amino-lower-alkyl)-2-lower-alkyl-3-(2-, 3- and 4-pyridylcarbonyl)-1H-indoles which are stated to possess fibrinolytic and anti-inflammatory activities.

Croce, Ann. di Chim. 63, 29–35 (1973) discloses 1-(3-aminopropyl)-3-benzoyl-2-methyl-1H-indole for which no utility is disclosed.

D'Ambra and Bell U.S. Pat. No. 4,840,950 discloses certain 4-arylcarbonyl-1-[(4-morpholinyl)-lower-alkyl]-1H-indoles useful as analgesics.

SUMMARY OF THE INVENTION

In a composition aspect, the invention relates to compositions for the treatment of glaucoma which comprise a pharmaceutical carrier and an effective intraocular pressure reducing amount of a 3-$R_3$-4-arylcarbonyl-1-[(4-morpholinyl)-lower-alkyl]-1H-indole or a pharmaceutically acceptable acid-addition salt thereof.

In a further composition aspect, the invention relates to 1-[2-(4-morpholinyl)ethyl]-4-(2-naphthylcarbonyl)-1H-indole and 3-methyl-4-(4-methoxybenzoyl)-1-[2-(4-morpholinyl)ethyl]-1H-indole useful as antiglaucoma agents.

In a method aspect, the invention relates to a method for the treatment of glaucoma which comprises administering to a patient requiring such treatment a composition containing, as the active ingredient, an effective intraocular pressure reducing amount of a 3-$R_3$-4-arylcarbonyl-1-[(4-morpholinyl)-lower-alkyl]-1H-indole or a pharmaceutically acceptable acid-addition salt thereof.

DETAILED DESCRIPTION OF THE PREFERRED EMBODIMENTS

More specifically, this invention relates to antiglaucoma compositions and to the method of use thereof in reducing intraocular pressure, said compositions containing as the active ingredient thereof, a 3-$R_3$-4-arylcarbonyl-1-[(4-morpholinyl)-lower-alkyl]-1H-indole having the structural formula:

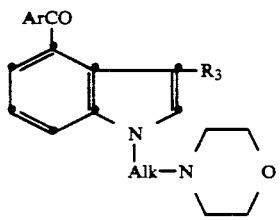

I where Ar is lower-alkoxyphenyl or 1- or 2-naphthyl, $R_3$ is hydrogen or lower-alkyl, and Alk is lower-alkylene containing from two to four carbon atoms.

Preferred compounds within the ambit of formula I as defined above are those where Ar is 4-lower-alkoxyphenyl or 1- or 2-naphthyl and Alk is 1,2-ethylene or 1,3-propylene.

As used herein the terms lower-alkyl and lower-alkoxy include, for example, methyl, ethyl, propyl, isopropyl, butyl, isobutyl, methoxy, ethoxy, propoxy, isopropoxy, butoxy and isobutoxy, and the term lower-alkylene includes straight or branched divalent lower-alkyl, for example, 1,2-ethylene, 1-methyl-1,2-ethylene, 2-methyl-1,2-ethylene, 1,3-propylene, 2-methyl-1,3-propylene, 3-methyl-1,3-propylene and 1,4-butylene.

The compounds of formula I are prepared by the method described in D'Ambra and Bell U.S. Pat. No. 4,840,950, the disclosure of which is incorporated herein by reference. As there disclosed, a 3-$R_3$-4-arylcarbonylindole of formula II hereinbelow is reacted with an appropriate 4-(halo-lower-alkyl)morpholine in the presence of a strong base, such as an alkali metal hydride or an alkali metal amide. The reaction is preferably carried out in an organic solvent inert under the conditions of the reaction, such as dimethylformamide (hereinafter DMF), toluene or xylene, and at temperatures from around ambient up to the boiling point of the solvent. A preferred base is sodium hydride, a preferred solvent is DMF, and it is preferred to carry out the reaction at the boiling point of the solvent.

The 3-$R_3$-4-arylcarbonylindoles of formula II where $R_3$ is hydrogen are in turn prepared by reaction of a 2-methyl-3-nitrobenzoyl halide with a lower-alkoxybenzene or naphthalene under Friedel-Crafts reaction conditions in the presence of aluminum chloride; reaction of the resulting 3-arylcarbonyl-2-methylnitrobenzene with DMF dimethyl acetal; and cyclization of the resulting 3-arylcarbonyl-2-(2-dimethylaminoethenyl)nitrobenzene by catalytic reduction.

The Friedel-Crafts reaction of a 2-methyl-3-nitrobenzoyl halide with a lower-alkoxybenzene or naphthalene is carried out in an organic solvent inert under the conditions of the reaction, such as methylene dichloride, ethylene dichloride, 1,1,2,2-tetrachloroethane or benzene. It is preferred to bring the reactants together at ambient temperature and then to heat the mixture at the boiling point of the solvent. A preferred solvent is methylene dichloride.

The reaction of the 3-arylcarbonyl-2-methylnitrobenzene with DMF dimethyl acetal is carried out by heating under reflux a solution of the former with a two to four molar excess of the latter in an organic solvent inert under the conditions of the reaction. Preferred solvents are DMF and dioxane.

The reductive cyclization of the 3-arylcarbonyl-2-(2-dimethylaminoethenyl)nitrobenzene is carried out in an organic solvent inert under the conditions of the reaction, for example ethyl acetate or a lower-alkanol, such as methanol, ethanol, or isopropanol, at ambient temperature and at hydrogen pressures in the range from around 50 to 100 p.s.i.g. Ethyl acetate or ethanol are preferred solvents, and it is preferred to carry out the reduction under a hydrogen pressure around 50 p.s.i.g. Preferred catalysts are palladium-on-charcoal or Raney nickel.

The overall synthetic sequence described above is represented by the reaction scheme:

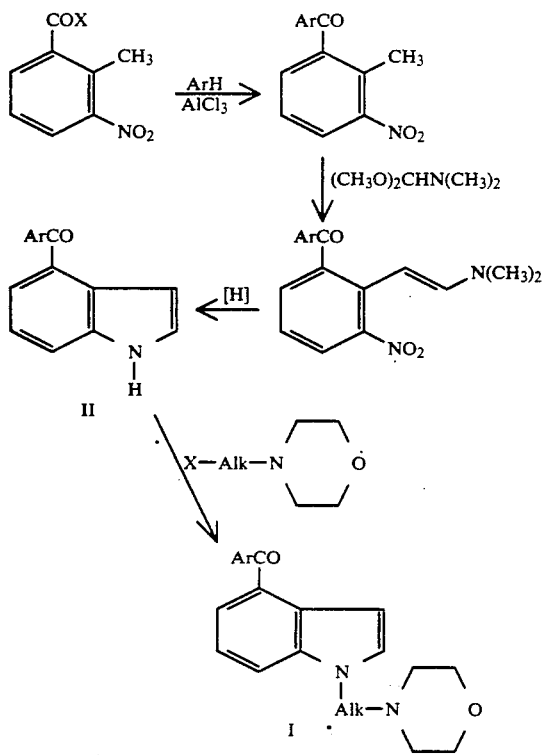

where X represents halogen and Ar and Alk have the meanings given above.

The compounds of formula II where $R_3$ is lower-alkyl are prepared by the Vilsmeier-Haack reaction by reacting the corresponding compound where $R_3$ is hydrogen with phosphorus oxychloride in DMF (to prepare the compounds where $R_3$ is methyl) or with phosphorus oxychloride and a lower-alkaneamide, an N-methyl-lower-alkaneamide or an N,N-dimethyl-lower-alkaneamide, $R'_3CON(R)_2$, where $R'_3$ is $C_1$-$C_3$ lower-alkyl and R can be hydrogen or methyl (to prepare the compounds where $R_3$ is $C_2$-$C_4$ lower-alkyl). [See Maheas, Bull. Soc. Chim. France 1989 (1962) and Bosshard et al., Helv. Chim. Acta, 42, 1659 (1959)]. The reaction is carried out at a temperature from 0° C. to 50° C. The resulting 4-arylcarbonyl-3-formylindole or 4-arylcarbonyl-3-lower-alkanoylindole is then reduced with an alkali metal cyanoborohydride to give the compounds where $R_3$ is lower-alkyl. The reduction is carried out in an acid medium at a pH in the range from about 2 to 5, in an organic solvent inert under the conditions of the reaction, such as lower-alkanols, THF, dioxane, diethyl ether or mixtures thereof.

The compounds of the invention in free base form can be converted to the acid-addition salt forms by interaction of the bases with an acid. In like manner, the free bases can be regenerated from the acid-addition salt forms in conventional manner, that is by treating the salts with cold, weak aqueous bases, for example alkali metal carbonates and alkali metal bicarbonates. The bases thus regenerated can be interacted with the same or a different acid to give back the same or a different acid-addition salt. Thus the novel bases and all of their acid-addition salts are readily interconvertible.

It will thus be appreciated that formula I not only represents the structural configuration of the bases of formula I but is also representative of the structural entity which is common to all the compounds of formula I, whether in the form of the free bases or in the form of the acid-addition salts of the bases. It has been found that, by virtue of this common structural entity, the bases of formula I and their acid-addition salts have inherent pharmacological activity of a type to be more fully described hereinbelow. This inherent pharmacological activity can be enjoyed in useful form for pharmaceutical purposes by employing the free bases themselves or the acid-addition salts formed from pharmaceutically acceptable acids, that is, acids whose anions are innocuous to the animal organism in effective doses of the salts so that beneficial properties inherent in the common structural entity represented by the free bases are not vitiated by side effects ascribable to the anions.

In utilizing this pharmacological activity of the salts, it is preferred, of course, to use pharmaceutically acceptable salts. Although water insolubility, high toxicity or lack of crystalline character may make some particular salt species unsuitable or less desirable for use as such in a given pharmaceutical application, the water-insoluble or toxic salts can be converted to the corresponding pharmaceutically acceptable bases by decomposition of the salts with aqueous base as explained above, or alternatively they can be converted to any desired pharmaceutically acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically acceptable free bases by reaction of the salts with aqueous base, or alternatively they can be converted to a pharmaceutically acceptable acid-addition salt by, for example, ion-exchange procedures.

The novel feature of the compounds, then, resides in the concept of the bases and the cationic form of the 3-$R_3$-4-arylcarbonyl-1-[(4-morpholinyl)-lower-alkyl]-1H-indoles of formula I and not in any particular acid moiety or acid anion associated with the salt form of the compounds; rather, the acid moieties or anions which can be associated with the salt forms are in themselves neither novel nor critical and therefore can be any acid anion or acid-like substance capable of salt formation with the bases.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride and the like.

The acid-addition salts are prepared by reacting the free base and the acid in an organic solvent and isolating the salt directly or by concentration of the solution.

In standard pharmacological test procedures the 3-$R_3$-4-arylcarbonyl-1-[(4-morpholinyl)-lower-alkyl]-1H-indoles of formula I have been found to possess cannabinoid receptor agonist activity and are thus indicated to be useful as anti-glaucoma agents.

It has been shown previously that smoking marijuana reduces intraocular pressure in man [Helper and Frank, Marijuana Smoking and Intraocular Pressure., J. Am. Med. Assoc. 217, 1392 (1971)]. Topical application or systemic injection of delta-9 tetrahydrocannabinol, a principal active ingredient in marijuana, also reduces intraocular pressure [Purnell and Gregg, delta-9 Tetrahydrocannabinol, Euphoria and Intraocular Pressure in Man., Ann. Opth. 7, 921-923 (1975); Green and Pederson, Effect of delta-9 Tetrahydrocannabinol on Aqueous Dynamics and Ciliary Body Permeability in the Rabbit Eye., Exptl. Eye Research 15, 499-507 (1973); Colasanti, Craig and Allara, Intraocular Pressure, Ocular Toxicity and Neurotoxicity after Administration of Cannabinol or Cannabigerol, Exptl. Eye Research 39, 252-259 (1984)]. Similarly, synthetic cannabinoids also reduce intraocular pressure [Green, Symunds, Oliver and Elijah, Intraocular Pressure Following Systemic Administration of Cannabinoids., Curr. Eye Research 2, 247-253 (1982); Tiedeman, Shields, Weber, Crow, Coccetto, Harris and Howes, Ophthalmology, 88, 270-277 (1981); Colasanti et al., supra]. Cannabinoid receptor binding sites can be defined as those to which radio-labelled 4-(1,1-dimethylheptyl)-2,3'-dihydroxy-6'alpha-(3-hydroxypropyl)-1',2',3',4',5',6'-hexahydrobiphenyl (CP 55940) binds in a specific and saturable manner and the binding sites are heterogeneously distributed in the brain [Devane Dysarz, Johnson, Melvin and Howlett, Determination and Characterization of a Cannabinoid Receptor in Rat Brain, Molecular Pharm. 34, 605-613 (1988)]. Natural and synthetic cannabinoids and representative examples of the compounds of the present invention, bind to CP 55940 binding sites. Classification of whether a molecule is an agonist or an antagonist can be made using a mouse vasa deferentia (MVD) preparation in vitro, compounds which inhibit contractions in the MVD preparation being considered active as agonists and those which do not inhibit contractions being considered antagonists. It is believed that agonist activity at the cannabinoid receptor mediates the anti-glaucoma actions of cannabinoids, and that agonist activity at this receptor correlates with ocular pressure lowering actions in man. Accordingly the cannabinoid receptor agonist activity of the compounds of the present invention indicate their usefulness in reducing ocular pressure and hence in treating glaucoma.

The 3-$R_3$-4-arylcarbonyl-1-[(4-morpholinyl)-lower-alkyl]-1H-indoles of formula I can be prepared for pharmaceutical use by incorporation of the compounds in unit dosage form as tablets or capsules for oral administration either alone or in combination with suitable adjuvants such as calcium carbonate, starch, lactose, talc, magnesium stearate, gum acacia and the like. Still further, the compounds can be formulated for topical or oral administration either in aqueous solutions of the water soluble salts or in aqueous alcohol, glycol or oil solutions or oil-water emulsions in the same manner as conventional medicinal substances are prepared.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus only be determined by the clinician after a consideration of all criteria and using his best judgment on the patient's behalf.

The molecular structures of the 3-$R_3$-4-arylcarbonyl-1-[(4-morpholinyl)-lower-alkyl]-1H-indoles were assigned on the basis of their infrared, ultraviolet and NMR spectra. The structures were confirmed by the correspondence between calculated and found values for elementary analyses for the elements.

The following examples will further illustrate the invention without, however, limiting it thereto. All melting points are uncorrected.

EXEMPLARY DISCLOSURE

Preparation of Intermediates

Preparation 1A

To a suspension of 95.6 g (0.716 mole) of aluminum chloride in 500 ml of methylene dichloride was added, rapidly and with stirring, a solution of 110.1 g (0.551 mole) of 2-methyl-3-nitrobenzoyl chloride in 400 ml of methylene dichloride. The mixture was then transferred to an addition funnel, added with stirring to a solution of 59.8 g (0.551 mole) of anisole over a thirty minute period, and the reaction mixture then heated under reflux for two hours. The mixture was decomposed by the careful addition, with stirring, of 1 liter of water and then filtered. The organic layer was separated from the aqueous layer, dried and taken to dryness, and the residue recrystallized from ethyl acetate to give 102.9 g of 3-(4-methoxybenzoyl)-2-methylnitrobenzene, m.p. 110°-113° C.

Anal., Calcd. for $C_{15}H_{13}NO_4$: C, 66.41; H, 4.83; N, 5.16. Found: C, 66.33; H, 4.95; N, 4.98.

Preparation 1B

Following a procedure similar to that described in Preparation 1A above, 71.1 g (0.554 mole) of naphthalene in 500 ml of methylene dichloride was treated, over a thirty minute period with stirring, with a mixture of 110.5 g (0.554 mole) of 2-methyl-3-nitrobenzoyl chloride and 96.0 g (0.72 mole) of aluminum chloride in 900 ml of methylene dichloride. The crude product isolated from the reaction mixture crystallized from ethyl acetate/hexane. The crystals so-obtained were recrystallized again from ethanol to give material having m.p. 100°-102° C. which, from its nmr spectrum and analyses for the elements, was identified as 2-methyl-3-(2-naphthylcarbonyl)nitrobenzene (45% yield).

The combined mother liquors from the isolation of the 2-naphthyl isomer were taken to dryness and the resulting oil crystallized from toluene/hexane to give material which, from its nmr spectrum, was identified as 2-methyl-3-(1-naphthylcarbonyl)nitrobenzene in about 30% yield.

Preparation 2A

A solution of 97.9 g (0.36 mole) of 3-(4-methoxybenzoyl)-2-methylnitrobenzene and 191 ml (1.45 mole) of DMF dimethyl acetal in 400 ml of DMF was heated under reflux for about nineteen hours and the reaction mixture then taken to dryness in vacuo to give 108 g of 2-(2-dimethylaminoethenyl)-3-(4-methoxybenzoyl)nitrobenzene as a red oil.

Preparation 2B

Following a procedure similar to that described in Preparation 2A above, 57 g (0.195 mole) of 2-methyl-3-(1-naphthylcarbonyl)nitrobenzene and 103 ml (0.784 mole) of DMF dimethyl acetal in 300 ml of DMF was heated under reflux for seventeen hours and then taken to dryness to give 2-(2-dimethylaminoethenyl)-3-(1-naphthylcarbonyl)nitrobenzene as an oil.

Preparation 2C

Following a procedure similar to that described in Preparation 2A above, 58.4 g. (0.20 mole) of 2-methyl-3-(2-naphthylcarbonyl)nitrobenzene and 106 ml. of (0.80 mole) of DMF dimethyl acetal in 250 ml. of DMF was heated under reflux for about eighteen hours and then taken to dryness to give 74.5 g. of 2-(2-dimethylaminoethenyl)-3-(2-naphthylcarbonyl)nitrobenzene as a red oil.

Preparation 3A

A solution of 32 g. (0.098 mole) of 2-(2-dimethylaminoethenyl)-3-(4-methoxybenzoyl)nitrobenzene in 200 ml of ethyl acetate was treated with 5 g of 10% palladium-on-charcoal, and the starting material reduced with hydrogen under 50 p.s.i.g. The mixture was then filtered, the filtrate taken to dryness, and the residue recrystallized from ethyl acetate to give 18.1 g of 4-(4-methoxybenzoyl)indole. Another sample, similarly prepared by reduction of the starting material with Raney nickel in ethanol, afforded material having m.p. 148°-152° C.

Anal., Calc. for $C_{15}H_{11}NO$: C, 76.48; H, 5.21; N, 5.57. Found: C, 76.73; H, 5.27; N, 5.58.

Preparation 3B

Following a procedure similar to that described in Preparation 3A above, 72 g (0.21 mole) of 2-(2-dimethylaminoethenyl)-3-(1-naphthylcarbonyl)nitrobenzene was reduced with hydrogen over 13.5 g of 10% palladium-on-charcoal in ethyl acetate under 40 p.s.i.g. Removal of the catalyst by filtration and evaporation of the filtrate to dryness afforded 45 g of 4-(1-naphthylcarbonyl)indole as an oil, which was used as such in Example 1C without further purification.

Preparation 3C

Following a procedure similar to that described in Preparation 3A above, 74.5 g. (0.215 mole) of 2-(2-dimethylaminoethenyl)-3-(2-naphthylcarbonyl)nitrobenzene was reduced by refluxing a solution thereof in 800 ml. of ethanol over ten heaping spoonfuls of Raney nickel for about twelve hours. Removal of the catalyst by filtration and evaporation of the filtrate to dryness afforded 15 g. of 4-(2-naphthylcarbonyl)indole as an oil which was used as such in Example 1D without further purification.

Preparation 3D

To 3 liters of DMF was added, dropwise with stirring and cooling to 0° C., 58.4 ml. of phosphorus oxychloride. The solution was then treated, dropwise with stirring and cooling to 10° C., with a solution of 38.9 g. (0.155 mole) of 4-(4-methoxybenzoyl)indole in 150 ml. of DMF and stirred at 35° C. for one hour. The mixture was treated cautiously with 200 g. of crushed ice and 150 ml. of water, basified by the careful addition of a solution of 254 g. of sodium hydroxide in 650 ml. of water, heated under reflux and cooled to ambient temperature. The solid which separated was collected and partitioned between MDC and water. The organic layer was washed with water, dried and taken to dryness and the residue recrystallized from ethyl acetate to give 31.2 g. of 3-formyl-4-(4-methoxybenzoyl)indole, m.p. 164°-167° C.

The latter (19.8 g., 0.071 mole) was dissolved in 600 ml. of THF and 500 ml. of methanol containing bromocresol green indicator, and 10.8 g. (0.17 mole) of sodium cyanoborohydride was added. The mixture was treated dropwise with stirring with a solution of hydrogen chloride in methanol at a rate sufficient to maintain the pH around 3. The mixture was then taken to dryness in vacuo and the residue chromatographed on silica gel, eluting with 4:1 hexane:ethyl acetate. There was thus obtained about 9 g. (49%) of 4-(4-methoxybenzoyl)-3-methylindole, m.p. 130°-132° C.

Preparation of the Final Products

Example 1A

To a stirred mixture of 3.5 g (0.0887 mole) of a 60% suspension of sodium hydride in hexane in 50 ml of DMF was added 18.1 g (0.0721 mole) of 4-(4-methoxybenzoyl)indole. The mixture was treated with a solution containing 0.18 mole of 4-(2-chloroethyl)morpholine in t-butyl methyl ether (prepared by extraction of the free base from a suspension of 35.5 g of the corresponding hydrochloride in saturated sodium bicarbonate). When addition was complete, the reaction mixture was heated under reflux for about twelve hours, treated with 1500 ml of water and extracted with 500 ml of ethyl acetate. The combined organic extracts, on drying and evaporation to dryness, afforded an oil which was dissolved in 250 ml of ethyl acetate and treated with 50 ml of ethereal hydrogen chloride. The material which separated was collected and recrystallized from ethanol to give 20.3 g of 4-(4-methoxybenzoyl)-1-[2-(4-morpholinyl)ethyl]-1H-indole hydrochloride, m.p. 177°-180° C.

Anal., Cal. for $C_{22}H_{24}N_2O_3.HCl$: C, 65.91; H, 6.29; N, 6.99; Cl, 8.84. Found C, 66.23, H, 6.32; N, 7.18; Cl, 8.91.

Example 1B

Following a procedure similar to that described in Example 1A above, 10 g (0.0398 mole) of 4-(4-methoxybenzoyl)indole in 200 ml of DMF was alkylated with 16.3 g of 4-(3-chloropropyl)morpholine in the presence of 1.9 g (0.0478 mole) of a 60% suspension of sodium hydride in hexane. The product was isolated in the form of the hydrochloride salt to give 11.2 g of 4-(4-methoxybenzoyl)-1-[3-(4-morpholinyl)propyl]-1H-indole hydrochloride, m.p. 168°-171° C.

Anal., Calc. for $C_{23}H_{26}N_2O_3.HCl$: C, 66.58; H, 6.56; N, 6.75; Cl, 8.54. Found: C, 66.30; H, 6.61; N, 6.65; Cl, 8.73.

Example 1C

Following a procedure similar to that described in Example 1A above, 45 g (0.17 mole) of 4-(1-naphthylcarbonyl)indole in 500 ml of DMF was alkylated with about 0.425 mole of 4-(2-chloroethyl)morpholine (prepared by extraction of the free base into 200 ml of t-butyl methyl ether from a suspension of about 79 g of the corresponding hydrochloride in sodium bicarbonate) in the presence of about 10 g of a 60% dispersion of sodium hydride in hexane. The product was isolated in the form of the p-toluenesulfonate which was crystallized from ethyl acetate to give 5.3 g of 1-[2-(4-morpholinyl)ethyl]-4-(1-naphthylcarbonyl)-1H-indole p-toluenesulfonate hydrate 3:1, m.p. 86°-88° C.

Anal., Calc. for $C_{32}H_{32}N_2O_5S.1/3H_2O$: C, 68.31; H, 5.85; N, 4.98; S, 5.76. Found: C, 66.66; H, 5.15; N, 4.86; S, 5.67.

Example 1D

Following a procedure similar to that described in Example 1A above, 15 g. (0.05 mole) of 4-(2-naphthylcarbonyl)indole in 150 ml. of DMF was alkylated with about 0.125 mole of 4-(2-chloroethyl)morpholine in the presence of 3.2 g. (0.06 mole) of a 60% suspension of sodium hydride in hexane. The product was isolated in the form of the hydrochloride salt to give 5.9 g. of 4-(2-naphthylcarbonyl)-1-[2-(4-morpholinyl)ethyl]-1H-indole hydrochloride, m.p. 205°-210° C.

Anal., Calcd. for $C_{25}H_{24}N_2O_2.HCl$: C, 65.91; H, 6.29; N, 6.99; Cl, 8.84. Found: C, 65.92; H, 6.34; N, 7.05; Cl, 8.62.

Example 1E

Following a procedure similar to that described in Example 1A above, 8.2 g. (0.031 mole) of 4-(4-methoxybenzoyl)-3-methylindole in 100 ml. of DMF was alkylated with 0.077 mole of 4-(2-chloroethyl)morpholine (prepared by liberation of the free base from 14.4 g. of the hydrochloride salt) in the presence of 1.5 g. (0.037 mole) of a 60% dispersion of sodium hydride in hexane. The product was isolated in the form of the hydrochloride to give 8.8 g. of 4-(4-methoxybenzoyl)-3-methyl-1-[2-(4-morpholinyl)ethyl)-1H-indole hydrochloride, m.p. 209°-212° C.

BIOLOGICAL TEST RESULTS

The 3-$R_3$-4-arylcarbonyl-1-[(4-morpholinyl)-lower-alkyl]-1H-indoles of formula I were tested in the mouse vas deferens test and the CP 55490 binding assay. The results, expressed as the $IC_{50}$ in $\mu M$ (the inhibitory concentration which produces 50% of the maximum response), are given in the following table, the compounds being identified by the example number above where their preparations are described. Compounds are considered active in the MVD test at $IC_{50}$ levels of 5.0 $\mu M$ or less.

| Compound | MVD | CP |
|---|---|---|
| Ex. 1A | 0.076 | 0.444 |
| Ex. 1B | 0.033 | — |
| Ex. 1C | 0.003 | — |
| Ex. 1D | 0.163 | 0.363 |
| Ex. 1E | 5.0 | — |

I claim:
1. A method for the treatment of glaucoma which comprises administering to a patient in need of such treatment an effective intraocular pressure reducing amount of a compound having the formula:

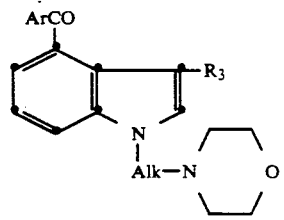

where Ar is lower-alkoxyphenyl or 1- or 2-naphthyl, $R_3$ is hydrogen or lower-alkyl, and Alk is lower-alkylene containing from one to four carbon atoms or a pharmaceutically acceptable acid-addition salt thereof.

2. A method according to claim 1 where Alk is 1,2-ethylene or 1,3-propylene.

3. A method according to claim 2 where $R_3$ is hydrogen.

4. A method according to claim 2 where $R_3$ is lower-alkyl.

5. A method according to claim 3 where the composition contains 4-(4-methoxybenzoyl)-1-[2-(4-morpholinyl)ethyl]-1H-indole or a pharmaceutically acceptable acid-addition salt thereof.

6. A method according to claim 3 where the composition contains 4-(4-methoxybenzoyl)-1-[3-(4-morpholinyl)propyl]-1H-indole or a pharmaceutically acceptable acid-addition salt thereof.

7. A method according to claim 3 where the composition contains 1-[2-(4-morpholinyl)ethyl]-4-(1-naphthylcarbonyl)-1H-indole or a pharmaceutically acceptable acid-addition salt thereof.

8. A method according to claim 3 where the composition contains 1-[2-(4-morpholinyl)ethyl]-4-(2-naphthylcarbonyl)-1H-indole or a pharmaceutically acceptable acid-addition salt thereof.

9. A method according to claim 3 where the composition contains 4-(4-methoxybenzoyl)-3-methyl-1-[2-(4-morpholinyl)ethyl]-1H-indole or a pharmaceutically acceptable acid-addition salt thereof.

* * * * *